United States Patent [19]
Gupta et al.

[11] Patent Number: 5,482,857
[45] Date of Patent: Jan. 9, 1996

[54] METHOD FOR REPRODUCING DOUGLAS-FIR BY SOMATIC EMBRYOGENESIS

[75] Inventors: Pramod K. Gupta, Federal Way, Wash.; Gerald S. Pullman, Alpharetta, Ga.

[73] Assignee: Weyerhaeuser Company, Tacoma, Wash.

[21] Appl. No.: 201,873

[22] Filed: Feb. 25, 1994

Related U.S. Application Data

[63] Continuation-in-part of Ser. No. 814,976, Dec. 23, 1991, Pat. No. 5,294,549, which is a continuation-in-part of Ser. No. 705,681, May 24, 1991, Pat. No. 5,236,841, which is a continuation-in-part of Ser. No. 499,151, Mar. 26, 1990, Pat. No. 5,036,007, which is a continuation-in-part of Ser. No. 321,035, Mar. 9, 1989, Pat. No. 4,957,866, and Ser. No. 426,331, Oct. 23, 1989, Pat. No. 5,034,326.

[51] Int. Cl.$^6$ .............................. A01H 4/00; A01H 7/00; C12N 5/01
[52] U.S. Cl. ................. 435/240.45; 435/240.4; 435/240.46; 435/240.49; 800/200; 800/DIG. 47; 800/DIG. 50
[58] Field of Search .................... 435/240.4, 240.45, 435/240.46, 240.49; 800/200, 205, DIG. 47, DIG. 50

[56] References Cited

U.S. PATENT DOCUMENTS

| | | | |
|---|---|---|---|
| 4,957,866 | 9/1990 | Gupta et al. | 435/230.4 |
| 5,034,326 | 7/1991 | Pullman et al. | 435/230.4 |
| 5,036,007 | 7/1991 | Gupta et al. | 435/240.45 |
| 5,187,092 | 2/1993 | Uddin | 435/240.45 |
| 5,236,841 | 8/1993 | Gupta et al. | 435/240.45 |

FOREIGN PATENT DOCUMENTS 0293598  12/1988  European Pat. Off. .

OTHER PUBLICATIONS

Becwar, M. R., R. Nagmani and S. R. Wann 1990 initiation of embryogenic cultures and somatic embryo development in lobloll pine (*Pinus taeda*). *Canadian Journal of Forestry Research* 20: 810–817.

Becwar, M. R., T. L. Noland and S. R. Wann 1987 A method for quantification of the level of somatic embryogenesis among Norway Spruce calluss lines. *Plant Cell Reports* 6: 35–38.

Durzan, D. J. and P. K. Gupta 1987 Somatic embryogenesis and polyembryogenesis in Douglas–fir cell suspension cultures. *Plant Science* 52: 229–235.

Ebert, A. and H. F. Taylor 1990 Assessment of the changes of 2,4–dichlorophenoxy–acetic acid concentrations in plant tissue culture media in the presence of activated charcoal. *Plant Cell, Tissue and Organ Culture* 20: 165–172.

Fridborg, Gunnar and Tage Eriksson 1975 Effects of activated charcoal on growth and morphogenesis in cell cultures. *Physiologia Plantarum* 34; 306–308.

(List continued on next page.)

*Primary Examiner*—Gary Bension

[57] ABSTRACT

The invention is a method for reproducing Douglas-fir by somatic embryogenesis using plant tissue culture techniques in a multistage culturing process. A suitable explant, typically the fertilized embryo excised from an immature seed, is first cultured on a medium that induces multiple early stage embryos. These are multiplied in a second culture having reduced growth hormones where the early stage embryos grow in size and vigor to advanced early stage embryos. The embryos may then be transferred directly to a cotyledonary embryo development culture containing an adsorbent such as activated charcoal. Preferably, they are first singulated by shaking in two or more liquid subcultures containing the adsorbent prior to placing them on the development medium. After several weeks somatic embryos having the appearance of zygotic embryos will have formed. These may be germinated before or after storage and transplanted to soil for further growth.

12 Claims, 2 Drawing Sheets

OTHER PUBLICATIONS

Gupta, Pramod K. and Don J. Durzan 1985 Shoot multiplication from mature trees of Douglas–fir (*Pseudotsuga menziesii*) and sugar pine (*Pinus lambertiana*). *Plant Cell Reports* 4: 177–179.

1986 Somatic polembryogenesis from callus of mature sugar pine embryos. *Bio/Technology* 4: 643–645.

1987 Biotechnology of somatic polyembryogenesis and plantlet regeneration in loblolly pine. *Bio/Technology* 5: 147–151.

Hakman, Inger, Larry C. Fowke, Sara von Arnold, and Tage Eriksson 1985 The Development of somatic embryos in tissue cultures initiated from immature embroyos of *Picea abies* (Norway spruce). *Plant Science* 38: 53–59.

Johansson, Lars 1983 Effects of activated charcoal in anther cultures. *Physiologia Plantarum* 59: 397–403.

Verhagen, Shirley A. and Steven R. Wann 1989 Norway spruce somatic embryogenesis: high–frequency initiation from light cultured mature embryos. *Plant Cell, Tissue and Organ Culture* 16: 103–111.

Nagmani, R. and R. J. Dinus 1991 Maturation of Douglas–fir somatic embryos in suspension culture. Paper delivered at the 21st Southern Forest Tree Improvement Conference, Knoxville, Tennessee, Jun. 17–20, 1991.

Nagmani, R., M. A. Johnson, and R. J. Dinus 1991 Effect of explant and media on initiation, maintenance, and maturation of somatic embryos in *Pseudotsuga menziesii* (*Mirb.*) *Franco* (Douglas–fir). In *Woody Plant Biotechnology*, M. R. Ahuja ed., pp. 171–178, Plenum Press, New York.

METHOD FOR REPRODUCING DOUGLAS-FIR BY SOMATIC EMBRYOGENESIS

This invention is a continuation-in-part of earlier application Ser. No. 814,976, filed Dec. 23, 1991 and now U.S. Pat. No. 5,294,549, which was a continuation-in-part of application Ser. No. 705,681, filed May 24, 1991 and now U.S. Pat. No. 5,236,841. That was a continuation-in-part of application Ser. No.499,151, filed Mar. 26, 1990, now U.S. Pat. No. 5,036,007. This was in turn a continuation-in-part of applications Ser. No. 321,035, filed Mar. 9, 1989, now U.S. Pat. No. 4,957,866 and Ser. No. 426,331, filed Oct. 23, 1989, now U.S. Pat. No. 5,034,326.

BACKGROUND OF THE INVENTION

The present invention is a method for reproducing coniferous plants by somatic embryogenesis using the techniques of plant tissue culture. More specifically, it relates to the reproduction of Douglas-fir (*Pseudotsuga menziesii* (Mirb.) Franco. The invention is especially suited for producing large numbers of clones of superior selections useful for reforestation.

Loblolly pine (*Pinus taeda* L.), its closely related southern pines, and Douglas-fir (*Pseudotsuga menziesii* (Mirb.) Franco) are probably the most important commercial species of temperate Noah American timber trees. Similarly, Norway spruce (*Picea abies* (L.) Karst.) is probably the most important European softwood species. Since the early 1940s, when serious private reforestation efforts began, literally billions of one and two year old nursery-grown trees have been planted on cut-over or burned forest lands. For many years these seedling trees were grown using as naturally produced seed from cones collected as a part time effort of individuals seeking to supplement their incomes. As early as 1957 forest geneticists began to plant seed orchards using either seed or grafted scions obtained from superior trees discovered in the forests. These trees were selected for such heritable characteristics as rapid growth, straightness of bole, wood density, etc. Now in both the southern pine and Douglas-fir regions the bulk of the seed is produced from selected trees grown in seed orchards, some of them now second and third generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

A brief review of some of the most important work relating to the present invention will follow. This is intended to be representative only and may not be fully inclusive of all the work in the field. Literature citations in the text are given in abbreviated form. Reference should be made to the bibliography at the end of the specification for full citations of the literature noted herein.

Culture by organogenesis is tedious and expensive due to the large amount of delicate manual handling necessary. It was soon recognized that embryogenesis was potentially a much more desirable method from the standpoints of quantity of plantlets produced, cost, potential genetic gain, and much lower probability of mutations. Work on embryogenesis of forest species began in the late 1970s. U.S. Pat. No. 4,217,730 to El-Nil describes one early attempt at somatic embryogenesis of Douglas-fir. This approach was later set aside because advanced stage embryos and plantlets could not be readily obtained. However, other workers entered the field in increasing numbers and progress has been rapid even if it has not until the present time reached the commercial stage.

Earlier U.S. Pat. Nos. 4,957,866, 5,034,326, 5,036,007, and 5,236,841, herein incorporated by reference describe improved methods of conifer embryogenesis. These also include extensive reviews of the most closely related literature. In the methods described in all of these patents, advanced early stage embryos (or "late stage proembryos"), defined as totipotent embryonic structures estimated to have least about 100 mostly undifferentiated cells, are transferred to and further cultured in a cotyledonary embryo development medium containing abscisic acid (ABA) as an essential growth hormone. It appears to be highly desirable during this stage to gradually reduce the level of exogenous ABA so that little or none is ultimately present. Other growth hormones: e.g., gibberellins, may also be used at this time. The ultimate product of this culturing step is somatic embryos resembling natural zygotic embryos in morphology.

It is well accepted that plant tissue culture is a highly unpredictable science. Söndahl et al., in published European Patent Application 293,598, speak directly to this point.

"Since each plant species appears to possess a unique optimal set of media requirements, the successful preparation and regeneration of a new species cannot be necessarily inferred from the successful regimens applied to unrelated plant species."

This statement can be carried even farther. Rangaswamy (1986) notes that the potential for embryogenesis is even genotype specific within any given species.

Compositions of the media used to initiate embryogenesis and induce embryo maturation are critical to success, regardless of the species being propagated. In particular, the type and level of the nitrogen source in the media and the presence or absence, composition, level, and timing of availability of growth hormones have been the key to success. It is also these very factors, particularly the hormones, that have proved to be so unpredictable. As one example, Ammirato (1977), conducted a study examining the effects of zeatin (a cytokinin), ABA, and gibberellic acid ($GA_3$) on the yield and morphology of caraway (*Carum carvi*) somatic embryos. These hormones were present singly and in all possible combinations in the media used for the later stages of embryo development. He concluded that a change in level or presence/absence of any one of the hormones caused a ripple effect felt throughout the system due to unpredictable interactions between the various hormones. Lakshmi Sita (1985) summarizes her earlier work and that of others in promoting embryogenesis of sandalwood (Santalum sp.). Gibberellic Acid was found to be useful in inducing embryogenesis using shoot explants in either solid or liquid suspension cultures. Despite her success, which included successful production of convened plants, she again points to the lack of predictability of embryogenesis.

"Despite progress, our knowledge of embryogenesis is still fragmentary. At present we cannot yet define the conditions necessary for embryogenesis . . . "

The same problem is again discussed by Evans (1984) who notes that growth hormones which affect the same process can either act independently or may interact in some fashion.

In general, as far as coniferous species are concerned, it appears that at least one exogenous auxin and usually a cytokinin are necessary hormones in a medium for the initiation of embryogenesis. To the present time it has also appeared necessary to include abscisic acid in the media for development of early stage embryos into cotyledonary stage embryos capable of germination and growth into plants. Douglas-fir, the subject species of the present invention, is known to have an embryogeny quite different from most other coniferous species. In the seed formation of most other conifers multiple embryos are present. Ultimately as the seed matures one embryo will become dominant and the others will either atrophy or be inactivated. However, in Douglas-fir only a single embryo is usually seen. This is discussed in some detail by Singh (1978). In actuality, Douglas-fir does appear to experience polyembryony very early in seed formation. However, all but one embryo is quickly suppressed. While the exact cause of this phenomenon is not known for sure, it appears to be related to a high level of endogenous abscisic acid (ABA) in the seed. Douglas-fir differs from other species as well during tissue culture. After initiation of early stage embryos, many of the embryos tend to form clumps of several individual embryos. Following the maintenance and multiplication stage, in the past these clumps have been separated into individual embryos by repeated transfers in liquid culture using media of relatively low osmolality. These "singulation" media initially required a relatively high level of exogenous abscisic acid which was reduced stepwise fashion in succeeding cultures. Ultimately, a very sharply raised osmolality and a relatively low level of ABA is needed in the cotyledonary embryo development culture. Even that low level of ABA is preferably continuously reduced by the presence of a hormone adsorbent such as activated charcoal. U.S. Pat. Nos. 5,034,326, 5,036,007, and 5,236,841 describe this process in considerable detail.

The use of activated charcoal as an additive in tissue culture has a long history. Fridborg and Eriksson (1975), citing even earlier workers, note the benefits of activated charcoal as used in their specific media. They comment as follows:

"It seems that the effects of activated charcoal are due to the removal of substances from the medium which promote unorganized growth, inhibit embryogenesis, root formation and elongation. One of these substances might be auxin . . . . "

More recently this statement has been made more emphatic. In a 1990 paper Ebert and Taylor stated:

"The addition of activated charcoal to both liquid and semi-solid media is a recognized practice in plant tissue culture. . . . [T]he most certain effect of adding AC to media is that of lowering the levels of plant growth regulators and other organic substances."

Most of the reported work using charcoal containing media has been on the various angiosperm species. As one example, Johansson (1983) found activated charcoal to strongly promote embryogenesis in anther cultures of *Anemone canadensis*. However, it is well established that a procedure that works well on one group of very closely related plants may be totally ineffective on unrelated plants. This is especially true when comparing plants as distantly related as those in different botanic Orders or Families. Success has been poor enough when using similar procedures between different members of the same genus.

In most tissue culture procedures, especially those involving conifers, activated charcoal has been used at the initiation stage of embryogenesis or for germination of cotyledonary stage embryos. On much rarer occasions it has been used in conifer embryogenesis in a single short duration subculture between the initiation and maintenance stages of culture. The three patents just listed above provide an exception where activated charcoal is used in the cotyledonary embryo development stage of culture to continuously reduce the level of abscisic acid in the medium.

Becwar, Nagmani, and Wann (1990), in work on loblolly pine, used activated charcoal in one of their initiation media and one maintenance medium. It was not used at the cotyledonary embryo development stage.

In a paper concerned mostly with initiation of embryogenic cultures of Norway spruce, Hakman, Fowke, von Arnold, and Eriksson (1985) noted that when cultured on a medium containing activated charcoal, embryos developed visible cotyledons and roots but this was only possible after the embryos had reached a certain stage of maturity. Since the exact procedures used by these workers was vague, it is unclear exactly when and how charcoal was used and whether it was or was not used in a cotyledonary embryo development stage.

In a paper published in 1985, Gupta and Durzan used activated charcoal in an elongation medium for sugar pine (*Pinus lambertiana*) buds in an organogenesis culture. These same authors in 1986 and 1987 papers described media containing activated charcoal in media for germination of somatic embryos of sugar pine and loblolly pine. Durzan and Gupta (1987) used the same treatment in the germination stage of Douglas-fir.

More recently, Becwar, Noland, and Wann (1987) and Verhagen and Wann (1989), working with Norway spruce, subcultured newly initiated embryogenic callus to a medium with 1% activated charcoal and lacking growth regulators for one week, followed by transfer to a maintenance medium consisting of their basal medium with 1 μm each of indolebutyric acid (IBA) and abscisic acid (ABA). Charcoal was not used elsewhere in their culturing procedure. A similar protocol was used by Uddin as described in U.S. Pat. No. 5,187,092.

Even with the knowledge of these reported instances of use of activated charcoal in conifer tissue culture media, it has not been at all apparent when it might be beneficial or detrimental nor has it been consistent in its expected results.

Techniques to promote embryogenesis of various members of several conifer genera are now well established. Research emphasis is now shifting to development of ways to scale up laboratory knowledge and techniques so that the process may become field operational on large scale. Yet many problems of a relatively fundamental nature still remain to be solved. One of these is improving somatic embryo quality and vigor and of reducing the cost. This is necessary so that germination to hardy plantlets and ultimate conversion to growing trees can be achieved at much higher percentages and much more economically than has heretofore been possible.

SUMMARY OF THE INVENTION

The present invention is directed to the use of activated charcoal for singulation of early stage Douglas-fir embryos taken from initiation or maintenance cultures and for further development of these embryos into vigorous cotyledonary embryos. It has been further discovered that a separate singulation stage is not absolutely essential before subculturing the early stage embryos onto a cotyledonary embryo development medium. By using the methods of the present invention the very expensive and heat labile abscisic acid heretofore found necessary at these stages of culture can be totally or substantially replaced by activated charcoal used in a specific manner.

The present method is especially suitable for reproducing woody gymnosperms of the order Coniferales. It is particularly well suited for generating large clones of superior forest trees reforestation, including species within the families Pinaceae, Cupressaceae, and Taxodiaceae. Most or all species within the genera Abies, Pinus, Picea, Tsuga, Pseudotsuga, Thuja, Juniperis, Larix, Taxus and Sequoia are believed to be amenable to multiplication by the present method.

The method is particularly advantageous in that it ultimately enables more robust somatic embryos to be produced. These have a high degree of similarity to the natural zygotic embryos produced within the seed. This results in higher numbers of embryos that can be successfully convened into plants growing in soil. Costs per plant can be significantly reduced over prior known tissue culture methods. In addition, use of the method generates early stage embryos that can be retained for extended periods of time in cryogenic storage. Alternatively, cotyledonary embryos are produced that can be held in cold storage for prolonged periods without the need to transfer them from the development medium.

A number of terms are known to have differing meanings when used in the literature. The following definitions are believed to be the ones most generally used in the field of botany and are consistent with the usage of the terms in the present specification.

"Activated charcoal" is a class of carbonized vegetable products or modified coal products which consists essentially of carbon modified to have extremely high surface areas and affinity for adsorption of various organic compounds from gaseous and liquid environments. When the term "charcoal" is used it should be read as meaning activated charcoal or an equivalent adsorbent material.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a translucent white mucilaginous mass that contains early stage embryos attached to suspensors. This is also referred to as an "embryonal-suspensor mass" or "ESM" by some investigators.

An "early stage embryo", also sometimes referred to before elongation of suspensor as a proembryo, is a small cell or mass of cells with dense cytoplasm and large nuclei that have the potential of forming a plant. The early stage embryo is normally found as a head having a relatively small number of undifferentiated dense cells with large nuclei associated at the end of one or more long thin-walled suspensor cells.

An "advanced early stage embryo" is larger than an early stage embryo and has a smooth embryonal head associated with multiple suspensor cells. The advanced early stage embryo is much more robust than an early stage embryo. Many investigators refer to these as "globular embryos". Advanced early stage embryos generally show no or only the initial stages of internal cell differentiation when sectioned.

A "cotyledonary embryo", sometimes simply referred to as an "embryo", has a well defined elongated bipolar structure with latent meristematic centers and has clearly visible cotyledonary primordia enclosing and usually obscuring an apical dome at one end with a latent radicle at the opposite end. The cotyledonary structure frequently appears as a small "crown" at one end of the embryo. A cotyledonary stage somatic embryo is morphologically analogous to a mature seed zygotic embryo.

A "mature embryo" is a cotyledonary embryo with adequate storage material (proteins, lipids, and carbohydrates) so as to be tolerant to desiccation.

An "explant" is a piece of tissue taken from a donor plant for culturing.

A "meristem" or "meristematic center" is a group of tissue forming cells capable of further development into plant organs; e.g., shoots and roots.

An "osmoticant" or "osmoticum" is a chemical material used for controlling the osmotic potential of a solution. In the present context the solution would be a culture medium.

A "plantlet" is a plant asexually reproduced by tissue culture.

A "converted embryo" is an embryo that has germinated and been established as a plant growing in soil.

"Somatic embryogenesis" is the process using tissue culture techniques for generating multiple embryos from an explant. The embryos generated from a given tissue source are believed to be genetically identical.

The present method as a whole comprises a multistage culturing process. A suitable explant is first placed on an induction or initiation culture medium. This will usually contain relatively high quantities of growth hormones including at least one auxin and frequently one or more cytokinins. However, with some species growth hormones at this initial stage may not always be necessary or desirable for induction of early stage embryos. A number of sources of explants have in the past proved to be satisfactory for culturing. These include, but are not limited to, tissue from cotyledons, hypocotyls, epicotyls, buds, meristematic centers for buds or roots, and seed embryos. Zygotic embryos removed from seeds are presently preferred. These may or may not include the surrounding gametophyte. In particular, for species which before have proved to be very difficult or impossible to propagate by somatic embryogenesis, the embryos from immature seeds may be preferred.

The first stage induction or initiation medium will normally be one of those well known from past work which contain a balanced concentration of inorganic salts and organic nutrient materials, with plant growth hormones included as noted above. Auxins are normally present in concentrations which may initially be as high as about 600 µM/L, more typically not exceeding about 500/µM/L. Cytokinins, if present, may initially be as high as 500 µM/L. The plant growth hormones may include at least one auxin and one cytokinin in a combined initial concentration not exceeding about 1100/μM/L, more typically not exceeding about 900/μM/L. The particular auxins and cytokinins used and their exact concentrations, or whether they are used at all, will depend somewhat on the species being cultured and even on the particular genotype within that species. This is something that cannot be easily predicted but can be readily determined experimentally. These very high levels of growth hormones assume the presence in the medium of an adsorbent material, such as activated charcoal. Where charcoal is not present the levels of growth hormones would normally be much lower; e.g., a full order of magnitude, than those just noted.

Culturing during the induction or initiation stage may be carried out in the dark, under very low light conditions, or in full light until an embryogenic mass forms. Lighting conditions will depend in large part on the composition of the particular medium selected. In general, initiation in full dark is preferred. This embryogenic mass has been described by various other names by researchers who have reported it in the past; e.g., embryogenic callus (Hakman and von Arnold 1985) or embryonal-suspensor mass (ESM) (Durzan and Gupta 1987). It has the appearance of a whitish, translucent, mucilaginous mass containing very small early stage embryos which are readily apparent by low power light microscopy. In the case of Douglas-fir the presence of activated charcoal or a similar adsorbent in the initiation medium appears to be advantageous. As was noted earlier, Douglas-fir does not experience polyembryony as do most other coniferous species. One hypothesis suggests that Douglas-fir seeds contain a high endogenous level of abscisic acid which suppresses polyembryony. Activated charcoal in the initiation medium may remove this endogenous ABA, as well as undesirable metabolic byproducts, to allow polyembryony to occur in vitro. Because the charcoal will also gradually remove growth hormones over time the initial concentrations of these materials are necessarily higher than might otherwise be the case. The preferred induction medium for Douglas-fir will preferably contain an auxin or auxins in amounts of about 400–600/ μM/L and a cytokinin or cytokinins in the amount of about 240–500 μM/L in combination with 0.05–1.0 % activated charcoal.

Early stage embryos from the initiation culture are normally transferred to a maintenance and multiplication medium of higher osmotic potential than the induction medium. This multiplication medium will typically have the concentration of plant growth hormones significantly reduced below that of the induction medium. By "significantly reduced" is meant lowered by a factor which may typically be one whole order of magnitude. In the case of Douglas-fir it may be two full orders of magnitude below that initially present in a charcoal containing induction medium. No hormone adsorbent is usually necessary or desirable at this time. Especially for species such as loblolly pine (*Pinus taeda*) and Douglas-fir (*Pseudotsuga menziesii*) the osmotic potential of the maintenance medium should be significantly increased over that of the induction medium. Levels of about 170–180 mM/kg minimum will suffice for most genotypes of Douglas-fir. One advantage of this osmotic "pulse" is that it contributes to embryo quality and size with the development of advanced early stage embryos. Weekly subcultures are usually made when the embryos are on maintenance medium. Incubation at this stage is usually carried out in the dark or in greatly reduced light until robust advanced early stage embryos have formed.

Douglas-fir embryos are then preferably transferred to a singulation medium but may be transferred directly to a cotyledonary embryo development medium, both of which usually entirely lack auxins and cytokinins.

Many investigators refer to cotyledonary embryo development from early stage embryos simply as a "maturation" or "development" stage. That usage will be understood herein unless the word "development" is otherwise qualified.

As was just noted, while not absolutely essential, Douglas-fir should preferably have an intermediate culturing step between the advanced early stage embryo growth stage and the final cotyledonary embryo development stage. With this species many of the embryos form in tight clumps or clusters. Singulation is carried out in a series of liquid shake cultures lacking auxins and cytokinins. The osmotic potential level is reduced from that of the maintenance medium, being in the range of 130–160 mM/kg. Previous to the discoveries of the present invention, the singulation process usually encompassed about three transfers at weekly intervals using liquid shake cultures. The initial treatment required ABA at a 10 mg/L level and was followed by two treatments with ABA at a 5 mg/L concentration.

Surprisingly, it has now been discovered that abscisic acid is not required for singulation. Two or three liquid shake subcultures in fresh medium at approximately weekly intervals are still used. However, it has now been found that activated charcoal, or another adsorbent that is its functional equivalent, in an amount of about 0.05–1.0%, preferably about 0.1–0.25 %, is as effective as the treatments using the very expensive hormone abscisic acid. The charcoal is preferably retained in a water permeable hydrophilic gel matrix insoluble in the medium. This can be in the form of a liquid over solid medium, in which the charcoal is in a continuous solid phase, normally located as a layer on the bottom of the culture flask. A preferred system uses the charcoal retained within small individual pellets or balls. These usually fall within the range of about 0.5–5 mm in diameter, most typically 2–3 mm. An insolubilized alginate gel has proven to be very satisfactory but other well known hydrophilic gel materials are also suitable.

Further development and enlargement of the embryos will occur during the singulation stage for Douglas-fir. Some internal differentiation of cellular structure may begin to be seen in embryos at the end of the singulation stage. The embryos at this point can be considered to be advanced early stage embryos or even slightly beyond this stage of embryogeny.

Another related but unexpected discovery of the effectiveness of charcoal for singulation is that embryos from the maintenance stage may be placed directly on a hormone-free cotyledonary embryo development medium containing activated charcoal. Singulation and further growth will normally occur in a satisfactory manner without the necessity of using the liquid shake singulation series of cultures following maintenance stage. While this method is not presently preferred because the resulting embryos tend to smaller due to competition from greater numbers, nevertheless it is perfectly suitable for growth of cotyledonary embryos that can later be germinated into plantlets.

Whether or not the singulation stage has been employed, a cotyledonary embryo development medium is necessary for growth of robust embryos having a high percentage of survival during germination. It is most desirable for the final development stage or stages to be carried out on either a solid medium or with a liquid medium using a pad system. For reasons not perfectly understood, far more vigorous embryos are normally obtained when they are at least partially exposed to air in the final development stages.

If the singulation stage with activated charcoal has been employed prior to cotyledonary embryo development, the development medium may be one of three types. It may be conventional having both ABA and activated charcoal; e.g., as taught in U.S. Pat. No. 5,034,326. In this case charcoal will be present in an amount of about 0.025–5.0%, preferably 0.25–2.5%, and abscisic acid present in an amount of about 5–100 mg/L, most preferably about 10–50 mg/L. Alternatively, a low concentration of ABA alone may be used in an amount of about 0.25–5.0 mg/L. As a third alternative, charcoal alone may be used at a concentration of about 0.05–1.0%, preferably about 0.1–0.25%. In some cases where embryos have been previously singulated on charcoal-containing media, satisfactory cotyledonary embryo development can be carried out on a medium without either charcoal or ABA.

The osmotic potential of the cotyledonary development medium should be sharply raised above that of any of the preceding media. Initial levels may be in the 300–350 mM/kg range but these should be increased to levels of at least about 400 mM/kg as development proceeds. If development is started at levels around 300–350 mM/kg, the osmotic level may be increased during development by a complete medium change, a partial change in which some old medium is replaced, or by adding an appropriate from, such as a solution, of osmoticants to the medium without replacement of any of the original medium. Any of these changes may be considered a transfer to a "new" medium. With Douglas-fir, it is preferred that the osmotic levels at the end of the development period should be at least about 450 mM/kg although with some genotypes lower levels are acceptable. With most Douglas-fir genotypes initial osmotic levels of 600 mM/kg or even somewhat higher have given superior results. These higher levels tend to prevent deterioration, callusing, and greening of the embryos.

Osmotic potential in the later stages of cotyledonary development is best controlled by a combination of osmoticants. One of these should be a readily metabolized carbohydrate energy source, preferably a sugar such as sucrose, glucose, fructose, maltose, or galactose. Sucrose is a preferred ingredient and may be present in amounts in the range of 2–6%. The other is a poorly metabolized osmoticant of which sorbitol, lactose, or a polyalkylene glycol would be examples. In a solid development medium, a combination of sorbitol, lactose and polyethylene glycol has proved very effective. Polyethylene glycol (PEG) alone, in concentrations of about 15–30% of the medium, has worked very well in liquid development media. The molecular weight of the PEG is not critical and may fall in the range of several hundred to several thousand. PEG having a nominal molecular weight of about 8000 has proved to be very satisfactory. While the salts and organic components of the medium make a small contribution to the osmolality, the osmotic potential is primarily controlled by the carbon and energy-providing sugar and the other osmoticants. It is sometimes advantageous to use one combination of osmoticants at the beginning of development and transfer embryos to a medium having a different combination at some point during the development stage.

For virtually all coniferous species a supply of exogenous abscisic acid has in the past been regarded as an essential hormone and media component in the development from early stage embryos to cotyledonary embryos. As described in earlier U.S. Pat. Nos. 5,034,326 and 5,036,007, this was advantageously used in combination with an adsorbent, such as activated charcoal. The adsorbent was present in a sufficient amount and form to slowly reduce the abscisic acid level and remove metabolic waste products. It could not be present in such a high concentration as to deplete the abscisic acid in a very short time; e.g., in a matter of days. The combination of abscisic acid with the adsorbent usually required a higher initial concentration of abscisic acid than was the case if no adsorbent was present in the medium. Alternatively, ABA could be reduced in stepwise fashion as detailed in U.S. Pat. No. 5,236,841. Activated charcoal or other adsorbents are not necessary using the procedure of this patent. In the case of the present invention, where Douglas-fir is the subject species, it has now been found that ABA is generally not necessary for cotyledonary embryo development.

Following cotyledonary embryo development the embryos may be placed directly on a germination medium for conversion into plantlets. Alternatively, they may be converted into artificial seeds by any of a number of published processes.

The germination medium has no exogenous hormones, a lowered organic nitrogen content, and a reduced level of osmoticants. After a sufficient time in darkness followed by light, or a 16 hour light and 8 hour dark photoperiod, the cotyledonary embryos will have developed into plantlets. Douglas-fir does not absolutely require an initial dark period although an initial four day dark period is usually more satisfactory. The time period for germination will be about 1–2 months. The resulting plantlets will have a well developed radicle and cotyledonary structure with a growing epicotyl and are ready for planting in soil.

It is an object of the present invention to produce coniferous plantlets by somatic embryogenesis.

It is another object to produce a large clone of a genetically selected forest species for reforestation using the methods of somatic embryogenesis and plant tissue culture.

It is a further object to provide a method of somatic embryogenesis that will dependably and consistently provide coniferous plantlets in large quantifies.

It is yet another object to provide a method of somatic embryogenesis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantifies needed for reforestation.

It is also an object to provide a method that will produce somatic embryos in large quantities with improved robust morphology for conversion into plantlets.

It is a particular object to provide a method and suitable culture media for somatic embryogenesis that produces robust somatic embryos with a high percentage of conversion to plants growing in soil.

It still another object to provide a method that generates more robust advanced early stage embryos of improved morphology and vigor.

It is a principal object to provide a method of conifer tissue culture for Douglas-fir in which activated charcoal effectively performs many or all of the functions that formerly required abscisic acid in the culture media.

These and many other objects will become readily apparent to those skilled in the art by reading the following detailed description, taken in conjunction with the drawings.

BRIEF DESCRIPTION OF THE DRAWINGS

The figures show various stages of plant embryogenesis in which.

DETAILED DESCRIPTION OF THE PREFERRED EMBODIMENTS

Figure 1:
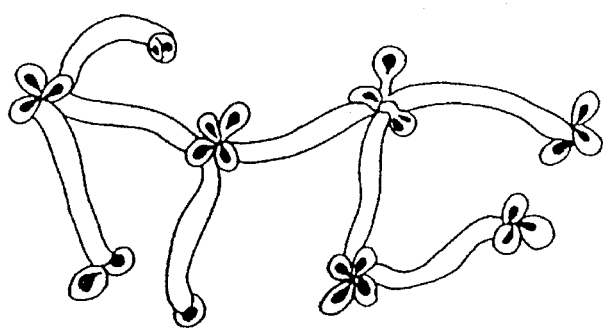
FIG. 1 shows early stage embryos.

The process of the present invention is not limited to any single basal culture medium or to the use of specific growth hormones other than those defined in the claims. Any of a number of well known basal media, such as that of Murashige and Skoog (1962), may be used. However, the present inventors have found the basal media described in Table 1 to give excellent results for culturing Douglas-fir (*Pseudotsuga menziesii*). The basal media are modified for each of the various culturing stages as shown in Table 2. A number of abbreviations are used in the following text. These are in common use in the field of tissue culture.

BAP—$N^6$-benzylaminopurine (or $N^6$-benzyladenine), a cytokinin.

KIN—kinetin (6-furfurylaminopurine), also a cytokinin 2,4—D-2,4-dichlorophenoxyacetic acid, an auxin NAA—2-naphthylacetic acid (naphthalene-2-acetic acid), also an auxin.

ABA—abscisic acid (5-(1-hydroxy-2,6,6-trimethyl-4-oxo-2-cyclohexen- 1-yl)-3-methyl-2,4-pentadienoic acid), a maturation promoter.

It will be understood by those skilled in the art that other plant growth hormones can be substituted for those just noted. As examples, IAA (indole-3-acetic acid), IBA (indole-3-butyric acid), and NAA (naphthalene-2-acetic acid) are effective auxins and 2–1P ($N^6$-isopentenylaminopurine) and zeatin are frequently used as cytokinins.

As an aid in comparing the present work with other published data, the following table of conversions from weight to molar concentrations might be useful.

|  | 1 µM/L | 1 mg/L |
| --- | --- | --- |
| BAP | 0.225 mg/L | 4.44 µM/L |
| KIN | 0.215 | 4.65 |
| 2,4-D | 0.221 | 4.52 |
| NAA | 0.816 | 5.38 |
| ABA | 0.264 | 3.78 |

One of the parents of the present application, U.S. Pat. No. 4,957,866, pointed out the importance of the control of osmotic potential of the media used in the various culturing stages. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereoisomeric/forms, such as scyllo-inositol are believed to be quite suitable. Among the sugars, sucrose, maltose, and glucose are known to be very effective and have been widely used in the past.

DOUGLAS FIR CULTURE

As noted in the background discussion of earlier U.S. Pat. No. 5.036,007, the embryogeny of Douglas-fir is quite different from trees such as the spruces or pines. One of these differences is seen when early stage embryos are placed in or on an advanced early stage embryo development medium. Douglas-fir tends to develop many tight clumps of these embryos in addition to a certain number of individual advanced early stage embryos. Upon further development into cotyledonary embryos, many of the clumped embryos remain united and the resulting product is difficult to work with for further conversion. This phenomenon had apparently been recognized earlier by Durzan and Gupta (1987) who, while they did not discuss it specifically, transferred their embryonal-suspensor masses to a liquid shake culture containing 0.5/µM abscisic acid. They note that under the influence of ABA, individual bipolar embryos were produced. These were then transferred to a development medium without ABA.

The present method most preferably utilizes a series of liquid shake cultures with reduced osmotic level and an added adsorbent such as activated charcoal between the maintenance and cotyledonary embryo development stages to achieve any necessary singulation. Other adsorbents such as activated alumina, silica gel, various natural and synthetic zeolites, and poly(vinylpyrrolidone) are believed to be useful as well as charcoal. The term "activated charcoal" should be considered in a generic sense for plant hormone adsorbents in general. While activated charcoal is the preferred adsorbent, it should be understood that when specific reference is made to it in the following examples other adsorbent materials such as those just noted should also be regarded as suitable. It is considered to be within the normal level of skill of those working in the an to make such substitutions.

Following singulation, osmotic level is raised to levels generally above about 450 mM/kg, preferably 600 mM/kg or even greater, during the final cotyledonary embryo development stage or stages.

Sorbitol (D-glucitol), D-mannitol, and galactitol (dulcitol) are straight chain sugar alcohols suitable as osmoticants. Lactose is a sugar effective as an osmoticant. Other materials suitable as osmoticants may include glycol ethers such as poly(ethylene glycol) and poly(propylene glycol) and their respective monomers.

While inorganic salts and pure simple organic chemicals generally behave similarly in culture media regardless of supplier, there are occasions when this is not the case for the more complex materials. Without intending endorsement of any product over available alternatives, chemicals from the following suppliers were used throughout the experiments to be described in the examples. Agar was obtained from Difco Laboratories, Detroit, Mich. Where specified as "tissue culture agar" the supplier was Hazleton Biologics, Inc., Lenexa, Kans. Casamino acids, a casein hydrolysate, was also supplied by Difco Laboratories. Activated charcoal was obtained from Sigma Chemical Company. St. Louis, Mo. as their grade NuC-4386.

A basal culture medium has been developed by the present inventors specifically to give more successful initiation and multiplication of Douglas-fir. Preferred media compositions are given in Tables I and 2. A number of ingredients may be varied in quantity, such as those that affect the level and balance between organic and inorganic nitrogen, depending on the response of individual genotypes. The media described are generally useful without further modification. However, the response of any given genotype cannot be readily predicted and any further media optimization must largely be achieved by a combination of intuition and trial and error.

TABLE 1

Pseudotsuga Menziesii Basal Culture Media

| Constituent | Concentration, mg/L | |
|---|---|---|
| | WTC[1] | BM$_G$[2] |
| BASAL SALTS | | |
| $NH_4NO_3$ | — | 206.3 |
| $KNO_3$ | varies[1] | 1170.0 |
| $CaCl_2.6H_2O$ | 200.0 | 220.0 |
| $Ca(NO_3)_2.4H_2O$ | varies[1] | — |
| $KH_2PO_4$ | 340.0 | 85.0 |
| $MgSO_4.7H_2O$ | 400.0 | 185.0 |
| $MnSO_4.H_2O$ | 20.8 | 8.45 |
| $ZnSO_4.7H_2O$ | 8.0 | 4.30 |
| $CuSO_4.5H_2O$ | 0.024 | 0.013 |
| $FeSO_4.7H_2O$ | 27.85 | 13.93 |
| $Na_2EDTA$ | 37.25 | 18.63 |
| $H_3BO_3$ | 5.0 | 3.10 |
| $NaMoO_4.2H_2O$ | 0.20 | 0.125 |
| $CoCl_2.6H_2O$ | 0.025 | 0.0125 |
| KI | 1.00 | 0.42 |
| ORGANIC ADDITIVES | | |
| myo-Inositol | varies[1] | 100.0 |
| Thiamine.HCl | 1.00 | 1.00 |
| Nicotinic acid | 0.50 | 0.50 |
| Pyridoxine.HCl | 0.50 | 0.50 |
| Glycine | 2.00 | 2.00 |
| L-Glutamine | varies[1] | 450.0 |
| Casamino acids | 500.0 | — |
| Sugar as specified | varies[1] | 20,000. |
| pH | 5.7 | 5.7 |

[1]Usage varies according to culturing stage and genotype.
[2]Modified Gupta and Durzan medium $BM_3$ (1986). Medium $BM_G$ of U.S. Pat. No. 5,034,326.

It will be seen by reference to the media compositions of the present invention that the features of the earlier inventions described in the patents previously noted are advantageously used here with Douglas-fir. A raised osmotic level following initiation is desirable for good quality advanced early stage embryo development. This level will differ somewhat between genotypes within each species as it does between species. If no singulation step is used and advanced early stage embryos are transferred directly to development media, the development media should contain an adsorbent such as activated charcoal. Normally no abscisic acid will be needed if the medium contains charcoal. In cultures where activated charcoal is used for singulation after maintenance, the development media may be one of three types. It may (1) contain only the adsorbent, (2) it may contain only relatively low levels of abscisic acid, or (3) it may contain both a hormone adsorbent and somewhat higher levels of abscisic acid. As a fourth alternative, some genotypes will require neither charcoal or ABA in the development medium.

The examples that follow represent the best mode known at present for culturing Douglas-fir according to the principles of the present invention. While the later examples are principally directed to singulation and cotyledonary embryo development stages, the steps prior to that time and following will first be briefly outlined in the following example, starting with initiation.

Example 1.

A preferred explant for Douglas-fir is an immature zygotic embryo with the gametophyte still attached. Best results have been realized with embryos selected in the interval just prior to the development of an apical dome up to the time just before cotyledon primordia become visible. The cones are split longitudinally and seeds isolated from young ovuliferous scales. Seeds are sterilized by first being agitated in

TABLE 2

| | Stage I Initiation | Stage II Maintenance 1 | Stage III Maintenance 2 | Stage IV Singulation | Stage V Development | Stage VI Germination |
|---|---|---|---|---|---|---|
| Basal Medium | WTC | WTC | WTC | WTC | WTC | $BM_G$ |
| $KNO_3$ | 1250[1] | 1250–2500 | 1250 | 1050 | 1000–2500 | 1170 |
| $Ca(NO_3)_2.4H_2O$ | — | — | — | 200 | — | — |
| myo-Inositol | 1000 | 5,000–10,000 | 5,000–10,000 | 100 | 100 | 100 |
| L-Glutamine | 450 | 450 | 1000 | 1000 | 750–1500 | — |
| Amino acid mixture[2] | — | — | — | — | 290 | — |
| Sugar | 15,000 | 30,000 | 30,000 | 20,000 | 20,000–60,000 | 20,000 |
| Supp. carbohydrate | — | — | — | — | 30,000–300,000 | — |
| 2,4-D | 110 | 1.1 | 1.1 | — | — | — |
| $N^6$-Benzyladenine | 45 | 0.22 | 0.22 | — | — | — |
| Kinetin | 43 | 0.22 | 0.22 | — | — | — |
| Abscisic acid | — | — | — | — | 0–50 | — |
| Gibberellins $GA_n$ | — | — | — | 0–15 | 0.5–25 | — |
| Activated charcoal | 2500 | — | — | 500–10,000 | 0–10,000 | 2500 |
| Agar | 5000 | 5000 | — | — | — | 8000[4] |
| Gelrite | — | — | — | — | 3000[3] | — |

[1]All units are in mg/L (or ppm).
[2]L-Proline - 100, L-Asparagine - 100, L-Arginine - 50, L-Alanine - 20, L-Serine - 20. The pH of all media are adjusted to 5.7.
[3]Not used for liquid media.
[4]Tissue culture agar.

In Table 2 sucrose is the sugar most commonly used in Stage I and Stages V and VI. In Stages I, III, and IV sucrose or maltose may be used. In general maltose has proved to give superior results to sucrose.

10% Liqui-Nox laboratory cleaner (Alconox, Inc, New York, N.Y.) with a small additional amount of liquid surfactant for about 10 minutes. They are then rinsed in running tap water for 30 minutes. At this time they are transferred to a sterile hood and agitated in 20% $H_2O_2$ for 10 minutes. Following five rinses in sterile deionized water the seed coat is split and the female gametophyte removed. This is split on one side and the embryo teased out while still remaining attached to the gametophyte by the suspensor. An explant so prepared is placed on the Stage I solid initiation medium in a 50 mm petri dish. The explants are incubated in the dark from 4–8 weeks. Success in forming an embryonal-suspensor mass (ESM) containing early stage embryos varies for reasons which are not well understood. Sucrose is the preferred sugar used in the initiation medium.

All stages of culture are carried out at temperatures which may vary between about 20°–25° C. Temperature is not generally critical and may, on occasion be varied so as to fall outside this range.

The embryonal-suspensor masses containing early stage embryos (FIG. 1) is then transferred to a solid Stage II maintenance and multiplication medium containing greatly reduced plant growth hormones and a significantly raised osmotic level. An osmotic level of at least about 170–180 mM/kg will usually suffice for Douglas-fir although some genotypes may require levels as high as 240 mM/kg. Myo-inositol, which will normally be around 5000 mg/L, may need to be adjusted somewhat depending on the needs of the particular genotype in order to obtain optimum results. Again, culturing is carried out in the dark with subcultures made at no greater than about two week intervals. The clone can be maintained at this stage for long periods of time.

Figure 2:
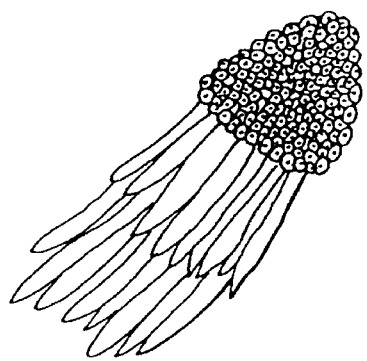
FIG. 2 shows advanced early stage embryos.

Early stage embryos from the Stage II multiplication step are then transferred to a liquid Stage III second maintenance medium having an osmotic level similar to that in the Stage II solid medium. Culture is carried out in the dark and subcultures are made periodically, usually weekly. Robust advanced early stage embryos estimated to have 100 or more cells (FIG. 2) will develop during this time, normally 5–6 weeks.

Following advanced early stage embryo development in Stage III, the cultures are most preferably transferred to a Stage IV liquid medium for singulation. The singulation medium has a reduced osmotic level and is free of auxins and cytokinins. Previously abscisic acid was used in a three stage treatment with 10 mg/L ABA in the first stage and 5 mg/L in the subsequent stages. In the present invention we have found that activated charcoal in an amount of 0.05–1.0%. preferably about 0.1–0.2% may be used to replace the expensive and heat labile ABA. Cultures are again carried out in the dark. From two to four subcultures in fresh media are made, preferably on a weekly basis.

After the final singulation treatment the embryos are rinsed with a fresh development medium from which most of the osmoticants have been removed before transfer to the cotyledonary development medium. A typical rinse medium would be a Stage V development medium lacking any PEG and with sucrose reduced to 2%. This would not contain any ABA or activated charcoal.

following the singulation period the embryos are ready to complete their development to cotyledonary embryos on a Stage V medium. They are transferred to either a solid medium or supported on a pad or bridge of filter paper using a liquid medium. In the past, this would normally have contained exogenous ABA. which would be present up to about 50 mg/L, along with about 0.1–5% of an adsorbent such as activated charcoal. More typically, ABA did not generally exceed about 10 mg/L and most usually did not initially exceed 5 mg/L and was often considerably lower. In some cases it was not necessary to add any exogenous ABA to the development medium since a sufficient amount would be carried over with the residual singulation or rinse medium accompanying the embryos when the transfer is made from the last singulation stage. The development medium in the past and presently may also contain from 0.5–50 mg/L of a selected gibberellin. This is preferably $GA_{4/7}$. $GA_3$ is also useful although it is somewhat less effective in most cases. Other active gibberellins would also be expected to be beneficial at this stage. Our commonly assigned copending application, Ser. No. 814,976, filed Dec. 20, 1991, gives details of the use of gibberellins and is hereby incorporated by reference. In cases where an adsorbent such as activated charcoal is not used in the development medium, concentrations of GA and ABA will be significantly lower than the maximum levels just noted; e.g., by a full order of magnitude.

It has been found preferable for Douglas-fir to carry out development cultures entirely in the dark. Activated charcoal is preferably used in the development medium to effect ABA reduction over time but it is not essential. Particularly for Douglas-fir, a raised osmotic level in the development medium is very highly desirable. Osmotic levels should be above about 400 mM/kg and for some genotypes may advantageously be considerably higher. The effect of osmotic level is discussed in detail in U.S. Pat. No. 5,036,007.

Figure 3:
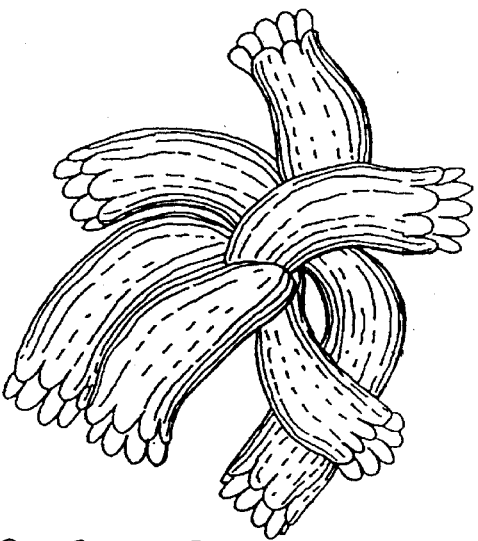
FIG. 3 depicts cotyledonary stage embryos.
Figure 4:
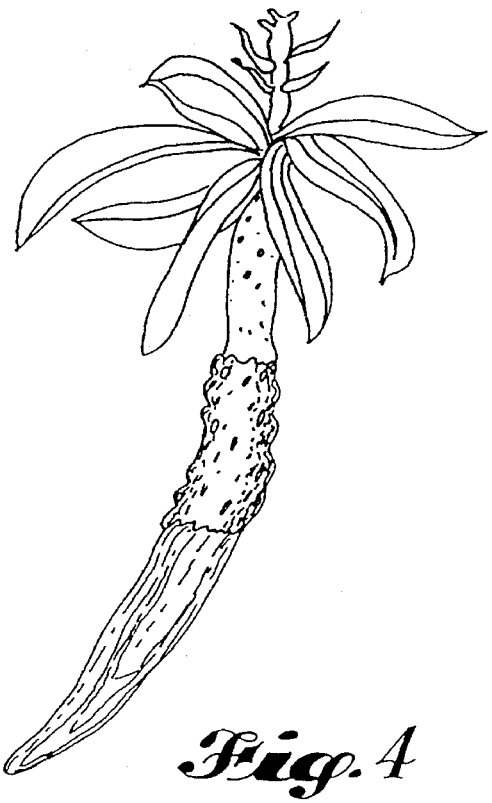
FIG. 4 shows a plantlet ready for transfer to soil.

Following the development stage the cotyledonary embryos (FIG. 3) may be placed on a Stage VI germination medium for production of plantlets (FIG. 4). Alternatively, they may be placed in artificial seeds for sowing in soil or other medium.

Example 2

An experiment was designed to show the results of taking Douglas-fir early stage embryos directly from a solid Stage II maintenance medium, using only a 10 minute dip treatment in Stage IV singulation medium having 0, 10, and 20 mg/L ABA, and then placing the dipped embryos directly on one of two Stage V development media The first development medium had 10 mg/L ABA with 1.25 g/L (0.125%) activated charcoal while the second lacked ABA and had 0.5 g/L (0.05%) charcoal. The development media both had 2% sucrose, 10% PEG 8000, and 1.25 g/L sorbitol for osmotic level control. Additionally, the development medium lacking ABA had 30 g/L lactose while the medium with ABA had only 25 g/L lactose. Both development media were solidified using 3 g/L Gelrite. The entire embryo colony was gently lifted from the maintenance medium, placed intact in the Stage IV singulation medium for 10 minutes, then placed on the development medium without rinsing. Five different Douglas-fir genotypes were used in the trial, each in replicate. Ratings were as follows:

0—No cotyledonary embryos
1—0.1–5 Cotyledonary embryos/cm$^2$
2—5–10 Cotyledonary embryos/cm$^2$
3—10+Cotyledonary embryos/cm$^2$ Results are as shown in Table 3 as averages of the replicates.

TABLE 3

| Dip Treatment ABA | Development Stage ABA | Rating Genotype 708 | Genotype 711 | Genotype 730 | Genotype 735 | Genotype 785 |
|---|---|---|---|---|---|---|
| 0  | 10 | 1.5 | 3*   | 0.5 | 0*   | 3   |
| 10 | 10 | 1   | 2.5* | 0   | 0*   | 1.5 |
| 20 | 10 | 1   | 2.5  | 0.5 | 0.5  | 1*  |
| 0  | 0  | 2   | 3    | 1.5 | 0*   | 1   |
| 10 | 0  | 3*  | 2.5  | 1.5 | 1    | 1.5 |
| 20 | 0  | 3*  | 2*   | 0.5 | 0.5* | 1.5 |

*indicates many precotyledonary embryos also present.

On reviewing the results of this trial it is evident that the development media lacking ABA and having only activated charcoal grew greater numbers of cotyledonary embryos than did the development media containing both ABA and activated charcoal. It is also clearly evident that as many cotyledonary embryos were produced in the cultures without any ABA in the dip treatment prior to development as were produced in those having the ABA dip. This shows that ABA is not necessary for Douglas-fir cotyledonary embryo development.

An experiment was conducted in which advanced early stage embryos from the Stage III medium, without a prior singulation treatment, were rinsed with development medium lacking PEG, ABA or charcoal and having only 2% sucrose. They were then placed directly on one of two solid development media. The first contained 0.1% activated charcoal while the second was similar except that it lacked charcoal. Neither medium had ABA. Three genotypes were tested in replicate. No cotyledonary embryos were produced on the medium lacking charcoal. The embryos of all three genotypes browned and died. However, cotyledonary embryos did develop on the charcoal containing medium. It is evident from this and the just reported example that either ABA or activated charcoal, or a combination of these, are necessary to produce satisfactory, cotyledonary embryos when no singulation stage is used.

Significant embryo singulation occurred on charcoal containing development media even though no prior singulation step had been used. A qualitative observation indicated that greater numbers of cotyledonary embryos had developed and, while these were viable, they tended to be smaller than those that had a singulation step. The reason for this is believed to be due to the fact that the embryos direct from maintenance are somewhat smaller than those at the end of a conventional singulation stage Since a constant volume of embryos was placed on the development medium in either case, apparently a greater number of the less mature embryos was transferred. This caused an unfavorable competitive situation resulting in the smaller embryos. However, the singulation noted on the development medium suggested the possibility of the use of activated charcoal in place of ABA in regular singulation medium. Initial experiments in which the powdered charcoal was added directly to the medium showed this indeed to be the case. A problem arose in that the charcoal tended to stick to the embryos and could not be readily rinsed off. This was remedied by one of two procedures. The first was to isolate the charcoal in a solid layer of medium in the bottom of the shake flask. The liquid medium containing the embryos was placed directly on top of the solid layer. In effect this created a two phase liquid-over-solid system. A second approach, which ultimately proved to be more satisfactory, was to encapsulate the charcoal in small hydrophilic gel pellets which were free to move about in the liquid during the shaking cycle. The following example describes preparation of one form of pelletized activated charcoal which has proved to be very satisfactory.

Example 4

Starting with 100 mL of Stage IV singulation medium lacking ABA, 1.5 g of the algin composition PROTONAL LF20/60® sodium alginate product was added and stirred several hours without heating until dissolved. PROTONAL LF20/60® is a registered trademark of and the product is available from Proton, Inc., North Hampton, N. H. To this was added 1.0 g of activated charcoal to give a 1.0% (or 10 g/L w/v) suspension. This was autoclaved to ensure sterility. A 0.1M solution (23.6 g/L) of calcium nitrate tetrahydrate was prepared and autoclaved separately. The alginate suspension of charcoal was added dropwise to the calcium nitrate solution with gentle stirring. Small balls of insolubilized charcoal-containing alginate about 2–3 mm in diameter were formed. These were thoroughly rinsed with sterile water and stored in a closed flask under refrigeration. Fifty of the charcoal balls added to 50 mL of culture medium are equivalent to 0.1% w/v activated charcoal.

Example 5

Figure 5:
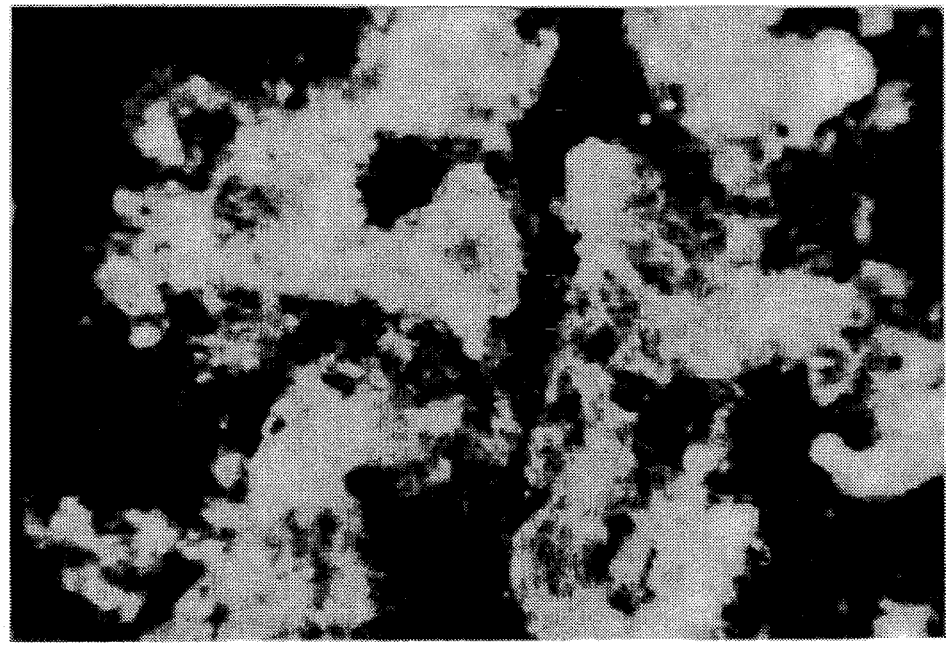
FIG. 5 is a photograph showing clumped early stage embryos.

5 mL of settled Douglas-fir cells from Stage III maintenance medium were placed in 50 mL of Stage IV singulation medium in a 250 mL Erlenmeyer flask. FIG. 5 is typical of the embryos from the maintenance medium showing the dumped embryos. Three genotypes were used in side-by-side replicated experiments. The stage IV medium lacked ABA but instead had 50 charcoal balls, as described in Example 3. After one week of culturing, subcultures were made to fresh medium with the charcoal treated as follows:

A. The original charcoal balls were reused.

B. The original charcoal balls were replaced with 50 new balls.

C. The original balls were reused and 50 new ones added.

Figure 6:
FIG. 6 is a photograph showing early stage embryos singulated by treatment with activated charcoal.

After an additional week of singulation, the embryos from the B. treatment above, in which both medium and charcoal balls were totally replaced, were the best singulated and had the largest heads of any of the treatments for two genotypes (732 and 925/2) (FIG. 6). Embryos from genotype 711 were less well singulated. A repeat of this experiment was made with genotype 711 using 100 charcoal balls (0.2% charcoal) in each of the singulation stages. This achieved singulation equal to that of the other genotypes which required only half of the amount of charcoal. It appears that singulation using activated charcoal is somewhat genotype sensitive with the exact amount of charcoal needed being best determined by simple experimentation.

The embryos from the "B" treatment above were rinsed with standard rinse medium (Stage V development medium lacking PEG and ABA and with only 2 % sucrose). They were then plated on regular Stage V cotyledonary embryo development medium with 19% PEG and 6% sucrose but lacking ABA. In one series 0.1% activated charcoal was added to the medium, A comparison series lacking charcoal was also run. The cotyledonary embryos produced using the charcoal-containing medium were fully equivalent in appearance to those grown in the past using the more conventional ABA shake treatment for singulation and the ABA-charcoal containing development medium. The embryos grown on the development medium lacking either charcoal or ABA were of about the same quality but in significantly lower yield. Thus, it appears that early stage embryos singulated on charcoal-containing media will develop into cotyledonary embryos without either ABA or activated charcoal in the development medium. This was not the case when embryos were plated directly from the maintenance medium onto development medium. Then either charcoal or ABA, preferably both were necessary.

Example 6

A series of confirmatory experiments was performed in which embryos from Stage III maintenance medium were subjected to seven further treatments for development of cotyledonary embryos. These were as follows:

A. Embryos were subjected to a conventional three stage singulation treatment using 10/5/5 mg/L ABA then placed on a standard development medium containing 19% PEG, 6% sucrose, and 0.1% activated charcoal but lacking ABA. Osmolality of the development medium was about 660 mM/kg.
  B. Embryos were plated directly on a low osmolality development medium lacking PEG and with only 2% sucrose. This medium had 0.1% activated charcoal but lacked ABA. Osmolality was about 185 mM/kg.
  C. This treatment was similar to B. above except that three development media were used containing 2.5, 5.0, and 10.0 mg/L ABA respectively, all lacking any activated charcoal.
  D. Embryos were plated directly on development medium identical to that used in treatment A above, using 0.1% activated charcoal, but without an intervening singulation stage.
  E. This treatment was similar to that of D above except that three development media were used containing 2.5, 5.0, and 10.0 mg/L ABA respectively, all lacking activated charcoal.
  F. This treatment was similar to D and E above except that the development medium lacked both activated charcoal and ABA.
  G. Embryos were plated directly from maintenance on three conventional development media containing respectively 10, 25, and 50 mg/L ABA, each also containing 0.1% activated charcoal.

Thus, of the seven treatments only treatment A had a Stage IV singulation treatment. This was conventional in that it used ABA in the singulation media. Unless otherwise specified as in media B and C, all development media were in the range of 600–660 mM/kg osmolality.

Observations following the development period were as follows.

A. (Conventional singulation with charcoal containing development medium) —50–100 well singulated, well developed cotyledonary embryos.
  B. (Low osmolality development medium with charcoal) —very good advanced early stage embryo singulation but no cotyledonary embryos developed.
  C. (Low osmolality development media with ABA) —embryos singulated but browning occurred. No cotyledonary embryo development
  D. (Direct from maintenance to charcoal-containing development medium) —100–200 good quality cotyledonary embryos but singulation rather poor.
  E. (Direct from maintenance to ABA containing development media) —embryos clumped and callusing. Poor to no cotyledonary embryo development.
  F. (Direct from maintenance to development medium lacking both ABA and charcoal)—Embryos callused.
  G. Direct from maintenance to conventional development media with both ABA and charcoal) —Good singulation with many smaller sized cotyledonary embryos.

The results of trial D above are somewhat contradictory with those obtained in Example 2 where good singulation was obtained by plating directly from a Stage II solid maintenance medium onto a charcoal-containing development medium. The reasons for this are not clear and may relate to the somewhat different composition of the development medium of Example 2 or, more likely, to an insufficient amount of charcoal in the medium of the present example. The present example confirms the desirability, but not the absolute requirement, of a singulation stage between maintenance and development. Further, it confirms the need for control of ABA level in the development stage with that level being very low or zero at the end of the period. The need of Douglas-fir for a high osmotic level in development was previously well established and was similarly confirmed.

It should be recognized that there is not one single set of culturing conditions that will be suitable for achieving somatic embryogenesis of all species or fur all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the an of tissue culture. The procedures and formulations reported here have been somewhat modified over those reported earlier as more experience has been gained. They have given results that are far superior in terms of success and consistency than any processes reported heretofore.

it will be understood that many variations can be made in the procedures described for the various culturing stages while still remaining within the spirit of the present invention. It is the intention of the inventors that such variations should be included within the scope of their invention if found defined within the following claims.

BIBLIOGRAPHY

Abo El- Nil, Mostafa M.
1980 Embryogenesis of gymnosperm forest trees. U.S. Pat. No. 4,217,730.
Ammirato, Philip V.

1977 Hormonal control of somatic embryo development from cultured cells of caraway: interactions of abscisic acid, zeatin, and gibberellic acid. *Plant Physiology* 59: 579–586.

Becwar, M. R., R. Nagmani and S. R. Wann
1990 Initiation of embryogenic cultures and somatic embryo development in loblolly pine (*Pinus taeda*). *Canadian Journal of Forestry Research* 20: 810–817.

Becwar, M. R., T. L. Noland and S. R. Wann
A method for quantification of the level of somatic embryogenesis among
1987 Norway Spruce callus lines. Plant Cell Reports 6: 35–38.

Durzan, D. J. and P. K. Gupta
1987 Somatic embryogenesis and polyembryogenesis in Douglas-fir cell suspension cultures. Plant Science 52: 229–235.

Ebert, A. and H. F. Taylor
1990 Assessment of the changes of 2,4-dichlorophenoxyacetic acid concentrations in plant tissue culture media in the presence of activated charcoal. *Plant Cell. Tissue and Organ Culture* 20:165–172.

Evans, M. L.
1984 Functions of Hormones at the cellular level of organization. In *Hormonal Regulation of Development II*, Tom K. Scott Ed., pp 23–79, Springer-Verlag, N.Y.

Fridborg, Gunnar and Tage Eriksson
1975 Effects of activated charcoal on growth and morphogenesis in cell cultures. *Physiologia Plantarum* 34; 306–308

Gupta, Pramod K. and Don J. Durzan
1985 Shoot multiplication from mature trees of Douglas-fir (*Pseudotsuga menziesii*) and sugar pine (*Pinus lambertiana*). Plant Cell Reports 4:177–179.
Somatic polyembryogenesis from callus of mature sugar pine embryos. *Bio/Technology* 4: 643–645.
1987 Biotechnology of somatic polyembryogenesis and plantlet regeneration in loblolly pine. *Bio/Technology* 5: 147–151.

Gupta, Pramod K. and Gerald S. Pullman
1990 Method for reproducing coniferous plants by somatic embryogenesis. U.S. Pat. No. 4,957,866.
Method for reproducing coniferous plants by somatic embryogenesis using abscisic acid and osmotic potential variation. U. S. Pat. No. 5,036,007.
1993 Method for reproducing conifers by somatic embryogenesis using stepwise hormone adjustment. U.S. Pat. No. 5,236,841

Hakman, Inger, Larry C. Fowke, Sara von Arnold, and Tage Eriksson
1985 The development of somatic embryos in tissue cultures initiated from immature embryos of *Picea abies* (Norway spruce). *Plant Science* 38: 53–59.

Johansson, Lars
1983 Effects of activated charcoal in anther cultures. *Physiologia Plantarum* 59: 397–403.

Lakshmi Sita, G.
1985 Sandalwood (*Santalum album*). In *Biotechnology in Agriculture and Forestry* 1.*Trees* Y. P. S. Bajaj, ed., Springer-Verlag, N.Y.

Murashige, Toshio and Folke Skoog
1962 A revised medium for rapid growth and bio assays with tobacco tissue cultures. *Physiologia Plantarum* 15: 473–493.

Pullman. Gerald S. and Pramod K. Gupta
1991 Method for reproducing coniferous plants by somatic embryogenesis using adsorbent materials in the development stage media. U.S. Pat. No. 5,034,326.

Rangaswamy, N. S.
1986 Somatic embryogenesis in angiosperm cell tissue and organ cultures. *Proceedings Indian Academy of Sciences (Plant Sciences)* 96(4): 247–271.

Singh, Hardev
1978 *Embryology of Gymnosperms*, Chapter 11 *Embryo*. Gebrüder Borntrager. Berlin.

Söndahl, Maro R., T. B. Sereduk. Claudia M. Bellato, and Zhenghua Chen
1988 Somatic embryogenesis and plant regeneration of cacao. European Patent Application A 0 293 598.

Uddin. M. Rafique
1993 Somatic embryogenesis in gymnosperms. U.S. Pat. No. 5,187.092.

Verhagen. Shirley A. and Steven R. Wann
1989 Norway spruce somatic embryogenesis: high-frequency initiation from light cultured mature embryos. *Plant Cell, Tissue and Organ Culture* 16:103–111.

We claim:

1. A method of culturing singulated Douglas-fir somatic embryos by tissue culture in the absence of exogenous abscisic acid which comprises:

placing an explant on an initiation culture medium containing an auxin and cytokinin and growing a culture containing early stage embryos;

transferring the early stage embryos to a maintenance culture medium having a reduced level of auxin and cytokinin to further multiply and increase development of the early stage embryos; and then transferring the embryos to a cotyledonary embryo development medium lacking exogenous abscisic acid and having a plant hormone adsorbent sufficient to singulate any clumped embryos and cause further development of the early stage embryos into cotyledonary embryos.

2. The method of claim 1 in which the growth hormone adsorbent is activated charcoal in an amount of about 0.05–1.0%.

3. The method of claim 1 in which the cotyledonary development medium is entirely free of exogenous plant growth hormones.

4. A method of singulating any clumped early stage Douglas-fir embryos being propagated by tissue culture which comprises:

placing an explant on a first medium for initiation of early stage embryos, said initiation medium containing an auxin and a cytokinin;

transferring the early stage embryos for at least one subculture in a second medium for maintenance and multiplication, said second medium having a reduced level of auxins and cytokinins: and then transferring the embryos for at least two sequential subcultures in a third medium for singulation of any clumped embryos, said third medium lacking any auxins or cytokinins and being free of exogenous abscisic acid but containing a plant growth hormone adsorbent sufficient to effect singulation of the embryos during said subcultures.

5. The method of claim 4 in which the singulated embryos are then transferred to a cotyledonary embryo development medium to cause further development of the early stage embryos into cotyledonary embryos.

6. The method of claim 4 in which the plant growth hormone adsorbent in the singulation medium is activated charcoal in an amount of about 0.05–1.0%.

7. The method of claim 5 in which the cotyledonary embryo development medium also contains a plant growth hormone adsorbent.

8. The method of claim 7 in which the plant growth hormone adsorbent in the cotyledonary embryo development medium is activated charcoal in an amount of about 0.05–1.0%.

9. The method of claim 4 in which the medium for embryo singulation is a liquid medium.

10. The method of claim 9 in which the plant growth hormone adsorbent is present in the singulation medium enclosed in an gel matrix.

11. The method of claim 10 in which the plant growth hormone adsorbent is activated charcoal enclosed in an insolubilized alginate gel matrix.

12. The method of claim 11 in which the alginate gel matrix in the form of small balls having a diameter of about 0.5–5.0 mm.

* * * * *